United States Patent
Lorenzino et al.

(10) Patent No.: US 12,031,951 B2
(45) Date of Patent: Jul. 9, 2024

(54) METHOD FOR TESTING A DAMAGE TOLERANCE PROPERTY OF A PART MADE OF AN ALUMINIUM ALLOY

(71) Applicant: CONSTELLIUM ISSOIRE, Issoire (FR)

(72) Inventors: Pablo Lorenzino, Voiron (FR); Nicolas Bayona-Carrillo, Coublevie (FR)

(73) Assignee: CONSTELLIUM ISSOIRE (FR)

( * ) Notice: Subject to any disclaimer, the term of this patent is extended or adjusted under 35 U.S.C. 154(b) by 426 days.

(21) Appl. No.: 17/421,355

(22) PCT Filed: Dec. 19, 2019

(86) PCT No.: PCT/FR2019/053203
§ 371 (c)(1),
(2) Date: Jul. 7, 2021

(87) PCT Pub. No.: WO2020/144417
PCT Pub. Date: Jul. 16, 2020

(65) Prior Publication Data
US 2021/0396636 A1      Dec. 23, 2021

(30) Foreign Application Priority Data
Jan. 9, 2019 (FR) ........................... 1900193

(51) Int. Cl.
*G01N 3/08* (2006.01)
*G01N 33/20* (2019.01)

(52) U.S. Cl.
CPC ............... *G01N 3/08* (2013.01); *G01N 33/20* (2013.01); *G01N 2203/0067* (2013.01); *G01N 2203/0212* (2013.01)

(58) Field of Classification Search
None
See application file for complete search history.

(56) References Cited

U.S. PATENT DOCUMENTS

| | | | |
|---|---|---|---|
| 6,264,824 B1 * | 7/2001 | Reid ...................... | G01N 17/02 205/777 |
| 9,274,036 B2 * | 3/2016 | Malik .................... | G06N 3/084 |
| 2014/0229149 A1 * | 8/2014 | Guan ...................... | G06N 7/01 703/2 |

FOREIGN PATENT DOCUMENTS

| | | | | |
|---|---|---|---|---|
| CN | 108486508 A | * | 9/2018 | ............... C22F 1/04 |
| CN | 109142362 A | * | 1/2019 | ............. G01N 21/84 |

(Continued)

OTHER PUBLICATIONS

Kang, J.Y. et al. "Application of artificial neural network for predicting plain strain fracture toughness using tensile test results," Fatigue & Fracture of Engineering Materials & Structures, Feb. 27, 2006, pp. 321-329, vol. 29.

(Continued)

*Primary Examiner* — Peter J Macchiarolo
*Assistant Examiner* — Jermaine L Jenkins
(74) *Attorney, Agent, or Firm* — McBee Moore & Vanik, IP LLC (57) ABSTRACT

The invention involves a method for testing a damage tolerance property in an aluminum alloy part with the following steps:
  measure at least one property representative of a the part's tensile strength;
  use the property measured in step a) as input datum ($x_i$) of a neural network estimator;
  estimate, using the estimator, the representative property of the part's tensile strength; the method being characterized in that it includes:
consideration of an acceptance threshold and comparison of the property estimated at step c) to the acceptance threshold, taking into account a confidence interval;
based on the comparison:
  consider that the part passes the test;
  or consider that the part does not pass the test.

14 Claims, 9 Drawing Sheets

(56) References Cited

FOREIGN PATENT DOCUMENTS

| | | | | | |
|---|---|---|---|---|---|
| CN | 109142547 | A | * | 1/2019 | ......... G01N 29/4427 |
| CN | 106649964 | B | * | 2/2020 | ......... G06F 17/5009 |
| FR | 2761780 | A1 | * | 10/1998 | ............. G01N 29/14 |

OTHER PUBLICATIONS

Mulina, Anastasia et al., "Artificial Neural Network and Finite Element Modeling of Nanoindentation Tests," Metallurgical and Materials Transactions A, Jul. 2002, pp. 1939-1947, vol. 33A, No. 7.

"Aluminum and aluminum alloys—Terms and Definitions—Part 1: General Terms," Deutsches Institute for Normung, 2012, 1-180.

Abendroth, Martin et al., "Determination of deformation and failure properties of ductile materials by means of the small punch test and neural networks," Computational Materials Science, 2003, vol. 28, No. 3-4: 633-644.

A Fsc, "Inch Pound Department of Defense test method standard V 50 ballistic test for armor," Dec. 18, 1997, pp. 1-24. Retrieved from the Internet: URL:http://www.globalarmour.co.za/downloads/MIL_STD_662.pdf.

"Hot rolled weldable aluminum alloy sheets for armoring—Part 2: Ballistic testing method," Afnor French Testing Method, 2014, 1-16.

Rahman, Najihah Abdul et al., "Experimental and Numerical Investigation on the Layering Configuration Effect to the aminated Aluminum/Steel Panel Subjected to High Speed Impact Test," Metals, 2018, vol. 8, No. 732, 1-16.

Kilic, Namik et al. "Determination of penetration depth at high velocity impact using finite element method and artificial neural network tools," Defense Technology, 2015, pp. 110-122, vol. 11, ScienceDirect.

"Aluminum and aluminum alloys—Part 2: Sheet, strip, and plate: Mechanical properties," Swiss Mem, 2016, 1-100.

"Hot Rolled weldable aluminum alloy sheets for armoring—Part 3: Characteristics of the ammunitions and maximum protections velocities," Anfor French Testing Method, 2014, 1-2.

French Search Report of French Patent Application No. 1900193 dated Oct. 30, 2019.

International Search Report of International Patent Application No. PCT/FR2019/053203 dated Mar. 27, 2020.

Partheepan, G. et al., "Fracture toughness evaluation using miniature speciment test and neural network", Computational Materials Science, Jun. 12, 2008, pp. 523-530, vol. 44, No. 2.

"Standard Test Method for Linear-Elastic Plane-Strain Fracture Toughness Klc of Metallic Materials", Designation: E399-12E3, ASTM International, Dec. 31, 2013, pp. 1-33, West Conshohocken, PA, USA. Retrieved from the Internet: URL:http://www.astm.org/cgi-bin/resolver.cgi?E399-12E3.

"StandardTest Method for K-R Curve Determination", Designation: E561-10E2, ASTM International, Mar. 31, 2013, pp. 1-16, West Conshohocken, PA, USA. Retrieved from the Internet: URL:http://www.astm.org/cgi-bin/resolver.cgi?E561-10E2.

* cited by examiner

METHOD FOR TESTING A DAMAGE TOLERANCE PROPERTY OF A PART MADE OF AN ALUMINIUM ALLOY

CROSS-REFERENCE TO RELATED APPLICATIONS

This application is the National Stage entry of International Application No. PCT/FR2019/053203, filed 19 Dec. 2019, which claims priority to French Patent Application No. 1900193, filed 9 Jan. 2019.

BACKGROUND

Technical Field

The technical field of the invention is the testing of an aluminum alloy part, and in particular of parts intended to be used as structural elements of a vehicle or aircraft.

Description of Related Art

Aluminum alloys are routinely used in the aeronautical industry, in particular for the manufacture of structural or wing elements. Aluminum, by its light weight, its corrosion behavior and its ability to be shaped, meets the expectations of aeronautics. Its use in alloys makes it possible to obtain materials with improved mechanical properties. The alloys most commonly used in aeronautics are type 2XXX and 7XXX alloys.

The requirements of aircraft manufacturers relate to mechanical strength as well as damage tolerance, for example fracture toughness. Compliance with such requirements involves numerous experimental tests, with a view to characterizing and quantifying the mechanical properties. The aim is to ensure that the alloys meet the specifications imposed by the manufacturers.

Fracture toughness, which represents resistance to crack growth, is an important property in the case of aeronautical applications. Type AA2050 or AA2198 alloys exhibit, for example, particularly advantageous fracture toughness properties. The measurement of fracture toughness properties is governed by standards. For example, the ASTM E399-12 standard defines the determination of the critical value of the stress intensity factor, usually designated by the notation $K_{IC}$. This magnitude characterizes the resistance of a material to the sudden growth of a crack subjected to stresses such that the state of strain is planar. The acronym ASTM refers to the "ASTM International" standards body.

The magnitude $K_{IC}$ is usually determined experimentally, on a pre-cracked specimen. The test specimen is subjected to a stress according to which the surfaces of the crack move perpendicular to the crack plane, corresponding to a mode known as "opening mode", known to those skilled in the art by the designation "mode I".

On the other hand, the ASTM E561-10 standard lays out the definition of a curve, called the R curve, representing the effective stress intensity factor according to effective crack extension.

The critical stress intensity factor $K_C$, in other words the intensity factor which makes the crack unstable, is calculated from the R curve. The stress intensity factor $K_{CO}$ is also calculated by assigning the length of initial crack at the onset of the monotonic load, to the critical load. These two values are calculated for a test specimen of the required shape. $K_{app}$ represents the $K_{CO}$ factor corresponding to the test specimen used to perform the R curve test. $K_{eff}$ represents the $K_C$ factor corresponding to the test specimen which was used to perform the R curve test. $\Delta a_{eff(max)}$ represents the crack extension of the last valid point of the R curve. The length of the R curve—i.e. the maximum crack extension of the curve—is an important parameter in itself, especially for fuselage design. $K_{R60}$ represents the effective stress intensity factor for an effective crack extension $\Delta a_{eff}$ of 60 mm.

This experimental and destructive type of test, however, is time consuming.

Similarly, there is a need to estimate ballistic properties of products for weapons construction, in particular for armor plate components. Armor plate components can be used for the manufacturing of armor shell walls and supplementary inserts, which are removable panels fitted onto the external faces of vehicles. The armor panel has a face exposed to shocks and impacts, along with a rear or exit face. Upon impact on a metal armor panel, the armor-piercing projectile may be completely stopped by the panel, but damage to the panel on its rear face may result in the formation of fragments which are violently ejected from the panel inward. Impact capability is akin to damage tolerance. Armor panels are generally subjected to two types of tests. The first test, intended to quantify their ability to stop armor-piercing projectiles, is referred to by the letters "AP" ("Armor Piercing") and characterizes their puncture resistance. The second test aims to quantify their ability to withstand impacts that generate fragmented debris. This second type of test is referred to by the abbreviation "FSP" ("Fragment simulated projectiles"). During these tests, the armor panels are the target of projectiles of various shapes and sizes. For both tests, the ability to stop bullets and absorb their kinetic energy is quantified by a parameter called ballistic limit velocity (V50).

The determination of a product's ballistic limit velocity requires very specific means and accreditations, which make the tests long and expensive. There is thus a need to estimate the ballistic properties of products for construction in the armament industry.

The alloys most commonly used for armor plate are 2XXX, 7XXX, 5XXX and 6XXX series alloys.

Some authors have described methods for estimating damage tolerance properties by computational means. The publication by G. Partheepan "Fracture toughness evaluation using miniature specimen and neural network", Computational Materials Science 44 (2008) 523-530, describes the use of an estimator using a neural network to estimate a fracture toughness value in a non-destructive manner. The neural network was configured via a learning phase, during which diagrams, measuring elongation according to load using special test specimens of known fracture toughness, were established by modeling or by experimental measurements.

The publication by J Y Kang "Application of artificial neural network for predicting plain strain fracture toughness using tensile test results", Fatigue Fact Engng Mater 29, 321-329, also describes the use of an algorithm based on a neural network architecture to estimate a fracture toughness property from properties derived from tensile tests, in particular the yield strength, tensile strength, or elongation at rupture.

The aforementioned publications exploit the development of algorithms based on neural network architectures. Such algorithms are currently accessible in commonly used calculation software, for example the Matlab® environment or the Python environment.

The inventors propose a test method based on a non-destructive estimate of a damage tolerance value, so as to limit the number of destructive tests carried out on test specimens.

SUMMARY

One subject of the invention is a method for testing a damage tolerance property of a part made of aluminum alloy, the part being in the form of a sheet or of an extruded profile, comprising the following steps:
a) measure at least two properties resulting from tensile testing of the part, in the L (longitudinal) and/or ST (short transverse) and/or LT (long transverse) directions, the properties being chosen from:
  the yield strength;
  and/or the tensile strength;
  and/or the elongation at rupture;
b) take into account the thickness of the part;
c) use the properties measured during step a) along with the thickness taken into account during step b) as input parameters for a neural network estimator;
d) estimate, using the estimator, the property representative of a part's damage tolerance;
e) take into account an acceptance threshold and a confidence interval, and compare the property estimated during step d) to the acceptance threshold, taking into account the confidence interval;
f) based on the comparison:
  consider that the part passes the test;
  or consider that the part does not pass the test.

The term "damage tolerance" is understood to mean a property characterizing the resistance to the growth of cracks. This is the fracture toughness for example, this latter corresponding to a critical value of the stress intensity factor. Fracture toughness is in particular determined according to the protocol defined in standard ASTM E399-12. Another example of damage tolerance can be associated with puncture resistance, used in particular to characterize the performance of armor panels. For example, we can cite the ability to stop bullets and absorb their kinetic energy, which is quantified by a parameter called ballistic limit velocity (V50) defined according to NF A50-800 2 and 3 (2014).

By "taking into account the confidence interval" is meant for example that the confidence interval, possibly weighted by a weighting factor, is either added to the acceptance threshold or subtracted from the estimated property. This confidence interval does not correspond to a convergence criterion used to characterize the validity of the model in the estimator.

The terms "sheet" and "profiles" are defined in standard NF EN 12258-1.

According to one embodiment, when during step e), the part does not pass the test, the method comprises a step f) of measuring the damage tolerance property of the part from a test specimen taken from said piece.

The process may include one of the following characteristics, taken in isolation or according to technically feasible combinations:
step c) also includes consideration of a concentration of at least one alloying element in the aluminum alloy;
step a) comprises a measurement of the elongation at rupture and step c) includes consideration of the elongation at rupture thus measured;
step a) comprises a measurement of the yield strength and step c) involves consideration of the yield strength thus measured;
step a) also comprises a measurement of a hardness property and step c) involves consideration of the hardness property thus measured;
step a) comprises only a measurement of the elongation at rupture and the yield strength, step c) involves consideration of the elongation at rupture and the yield strength thus measured;
when step d) comprises an estimation of the property representative of a damage tolerance of the part according to the L-T (Longitudinal—Long Transverse) directions, step c) comprises, at the least, consideration of the properties measured during step a), in direction L;
when step d) comprises an estimation of the property representative of a damage tolerance of the part according to the T-L (Long Transverse—Longitudinal) directions, step c) comprises, at the least, consideration of the properties measured during step a), in direction LT;
when step d) comprises an estimation of the property representative of a damage tolerance of the part according to the S-L (Short Transverse—Longitudinal) directions, step c) comprises, at the least, consideration of the properties measured during step a), in direction ST.
step c) involves consideration of the properties measured during step a), in various directions.
step c) involves consideration of the three properties measured during step a), and this in three different directions, in particular directions L, ST and LT.
the damage tolerance property is an apparent intensity factor or a critical value of an intensity factor, also called fracture toughness.
the damage tolerance property is an effective stress intensity factor for a predetermined effective crack extension, for example 60 mm.
The damage tolerance property is a ballistic limit velocity (V50).
the aluminum alloy is an alloy of the 2XXX or 7XXX series, or of the 5XXX or 6XXX series.

Step c) can in particular be implemented by a processing unit, for example a microprocessor.

Other advantages and characteristics will emerge more clearly from the description that will follow of particular embodiments of the invention, given by way of non-limiting examples, and shown in the figures listed below.

BRIEF DESCRIPTION OF THE DRAWINGS

FIGS. 3A to 4C were established from estimates of the fracture toughness of type AA2050 aluminum alloys.

FIG. 5A shows results of damage tolerance measurements according to yield strength for different test samples. In FIG. 5A, the considered damage tolerance property is an effective stress intensity factor for an effective crack extension of 60 mm ($K_{R60}$).

DETAILED DESCRIPTION OF A PREFERRED EMBODIMENT

The critical stress intensity factor, denoted Kw, sometimes referred to as fracture toughness, is determined according to a test protocol defined in standard ASTM E399-12, mentioned in the prior art. A pre-cracked specimen is subjected to an increasing load. The crack has an opening, whose progression is measured according to the load applied to the test specimen. A curve, representing the load applied according to opening, is obtained, according to which a stress intensity factor $K_Q$ is determined, this latter corresponding to an intersection of the aforementioned curve and a line of predetermined slope. Under certain conditions, specified in paragraph 9 of the aforementioned standard, the stress intensity factor $K_Q$ corresponds to a valid measurement of the critical stress intensity factor $K_{IC}$. When these conditions are met, it is considered that the critical stress intensity factor $K_{IC}$ characterizes the material, being independent of the geometry of the test specimen considered. This magnitude, which corresponds to the fracture toughness in plane stress, is also referred to here simply by the term "fracture toughness".

The apparent stress intensity factor at break $K_{app}$, which corresponds to the fracture toughness in plane stress, is obtained by establishing a curve referred to by the term "R curve", according to a test protocol defined in standard ASTM E561. The R curve represents changes in the critical stress intensity factor $K_C$ for crack growth, according to crack length, under a monotonic and increasing stress. The R curve allows a determination of the critical load for an unstable break. A stress intensity factor $K_{CO}$ can also be determined by assigning an initial crack length, before the load is applied. The apparent stress intensity factor at break $K_{app}$ is the $K_{CO}$ factor corresponding to the test specimen that was used to establish the R curve. The $K_{R60}$ coefficient is the effective stress intensity factor for an effective crack extension of 60 mm.

The ballistic limit velocity is defined, for example, in the NF A 50-800-2 and 3 (2014) or MIL-STD-662 (1997) standards. This is the velocity at which the probability of armor plate penetration is 50%. The ballistic limit velocity is the mean of an even number of impact velocities, at least 4, half of which are protections, and the second half are non-protections. It is determined by calculating the mean velocity reached by the projectiles on impact resulting from taking the same number of results with the highest velocities corresponding to partial penetration and those results with the lowest velocities corresponding to complete penetration. Complete penetration occurs when the impacting projectile or any fragment (of the projectile or test specimen) pierces a thin control slab located behind the test specimen.

Structural element: a structural element of a mechanical construction is a piece for which static and/or dynamic mechanical properties are particularly important for the integrity of the structure. In an aircraft construction, these include, among others, the components of the fuselage, the wings, the tail unit and the vertical stabilizer.

In relation to the tensile tests, the terms sens travers, sens long (L), sens travers-long (TL), sens travers-court (TC) are defined in the NF EN 485 standard. They correspond respectively to the Anglo-Saxon designations Longitudinal (L), Long Transverse (LT or T) and Short Transverse (ST or S). In the following paragraphs, we shall use the acronyms L, LT and ST.

For damage resistance tests, the L-T, T-L and S-L directions are defined in standard ASTM E399-12, paragraphs 3.1.3.2 and 3.1.3.4. The first letter corresponds to a direction normal to the crack plane. The second letter corresponds to the crack growth direction. The following nomenclature is used in these designations: L=longitudinal; T=Long Transverse; S=Short Transverse.

The invention applies to aluminum alloys, and in particular to series 2XXX, 7XXX or 5XXX aluminum alloys. The alloys are named according to the nomenclature defined by The American Aluminum Association. The invention allows the testing of a piece made of aluminum alloy, and more precisely the testing of the part's damage tolerance property. The part can be a sheet, or some other type of part.

The invention takes advantage of a very large number of aluminum alloy parts having undergone precise mechanical or chemical characterizations, among which:
chemical composition;
thickness;
mechanical tensile properties, in particular the tensile yield strength, the ultimate tensile strength, the relative elongation, or the elongation at rupture;
properties representative of the damage tolerance, for example the fracture toughness ($K_{IC}$), the apparent intensity factor at break ($K_{app}$) or the intensity factor $K_{R60}$ or the ballistic limit velocity (V50) defined beforehand.

For example, the inventors had access to damage tolerance data relating to 6200 parts made of AA2050 type alloy, and this according to the LT, TL and ST directions. This represents very important characterization data. They also had tensile strength test data in the L, LT and ST directions.

Figure 1:
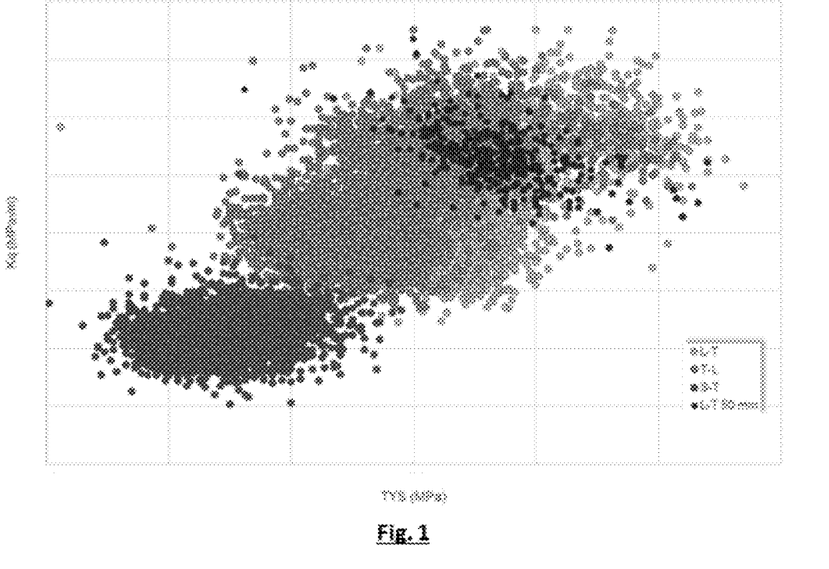
FIG. 1 shows, for different directions, results of fracture toughness measurements according to yield strength, for different test samples. Each point corresponds to a test sample. These results relate to AA2050 type aluminum alloys.

FIG. 1 shows a scatter plot, each point representing a test sample taken from a part. For each test sample, the fracture toughness ($K_{IC}$—ordinate axis) was represented according to the yield strength (abscissa axis). The gray level of each point corresponds to a direction as previously defined, the legend being as follows:
L-T: fracture toughness according to L-T, yield strength according to L;
T-L: fracture toughness according to T-L, yield strength according to LT;
S-T: fracture toughness according to S-T, yield strength according to ST;
L-T 50 mm: fracture toughness according to L-T, yield strength according to L—sheet thickness equal to 50 mm.

There is a degree of correlation between yield strength and fracture toughness.

The inventors have developed an algorithm for estimating properties characterizing the damage tolerance, according to input parameters representative of the tensile strength. For this, some of the characterization results available were used to form a learning set used to parameterize the algorithm. Another part of the available characterization results were used to form an algorithm test set after its parameterization.

80% of the available data were used to form the learning set. 20% of the available data were used to form the test set.

The algorithm used is a neural network consists of an input layer, comprising the input parameters $x_i$, an intermediate layer, or hidden layer, and an output layer, forming the magnitude to be estimated, in this case a damage tolerance property, e.g. fracture toughness. The intermediate layer forms a hidden layer, comprising $y_j$ nodes, or neurons. For each node $y_j$, and for each input datum $x_i$, there is a weighting factor $w_{i,j}$ determined during the learning phase. The inventors programmed the algorithm in the MATLAB® environment, software supplied by the company The Mathworks, by implementing the "ANN Toolbox" module. Learning serves to determine, among other things, the weighting factors of the hidden layer. In the example considered, the hidden layer has 30 nodes. Each node is linked to an input datum by a weighting factor and a bias.

Figure 2A:
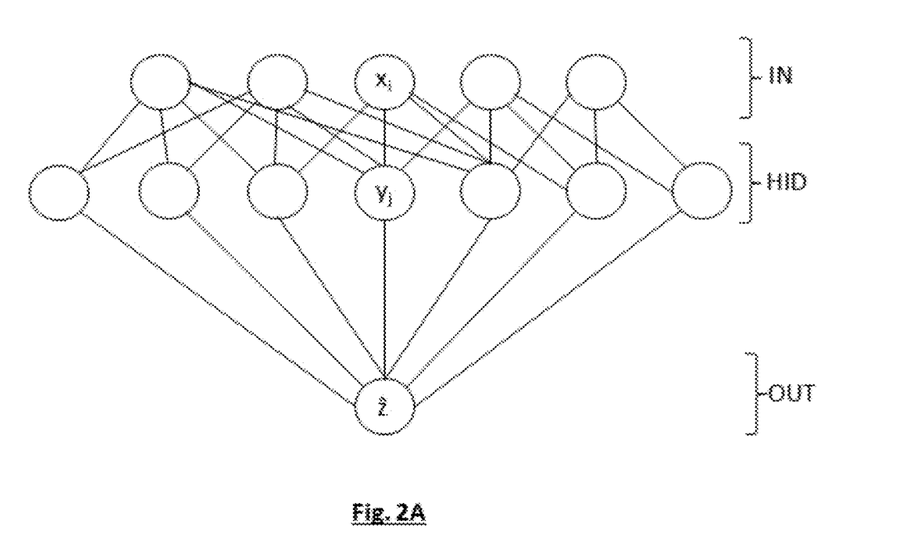
FIG. 2A is a schematic representation of a neural network architecture.

FIG. 2A is a schematic representation of the architecture of a neural network such as that implemented by the inventors. The network has 3 layers:
the input layer IN, comprising the input variables $x_i$. the index i is an integer between 1 and $N_i$, $N_i$ being an integer greater than or equal to 2. Each input variable is:
either a mechanical tensile property, in particular the relative elongation and/or the yield strength and/or the tensile strength;
or the thickness of the part;
or a mass fraction of an alloying element, for example a mass fraction of Cu or a mass fraction of Li.
the hidden layer HI, comprising nodes (or neurons) $y_j$. The index j is an integer between 1 and $N_j$, $N_j$ being an integer greater than or equal to 5 or 10. In this example $N_j=30$.
the output layer OUT, comprising an output variable $\hat{z}$. In our example, the output layer has only one output variable $\hat{z}$, which corresponds to the damage tolerance property estimated by the algorithm. This may be an estimate of the fracture toughness in plane stress ($K_{IC}$), but also of other parameters, for example the fracture toughness in plane stress $K_{app}$ or $K_{R60}$.

Each node of the intermediate layer is linked to each input datum. In FIG. 2A, not all the relationships have been shown, for the sake of clarity.

The algorithm is implemented by a data processing unit, for example a microprocessor, connected to a memory comprising the algorithm and its parameterization. The algorithm uses measured physical data, corresponding to the input parameters $x_i$ mentioned above.

Each node $y_j$ is assigned a weighting factor associated with an input variable $x_i$. Thus, each weighting factor is associated with an input datum $x_i$ and with a node $y_j$. Each node also has a bias value $w_{0,j}$. The weighting factors along with the bias $w_{0,j}$, of each node are determined during the learning phase. Each node $y_j$ implements an activation function $f_j$, such that:

[Math]

$$y_j = f_j\left(w_{0,j} + \sum_i w_{i,j} x_i\right) \quad (1)$$

In the architecture implemented by the inventors, each activation function $f_j$ is a hyperbolic tangent function. The values of each node $y_j$ are combined to form the value of the output variable $\hat{z}$.

Figure 3A:
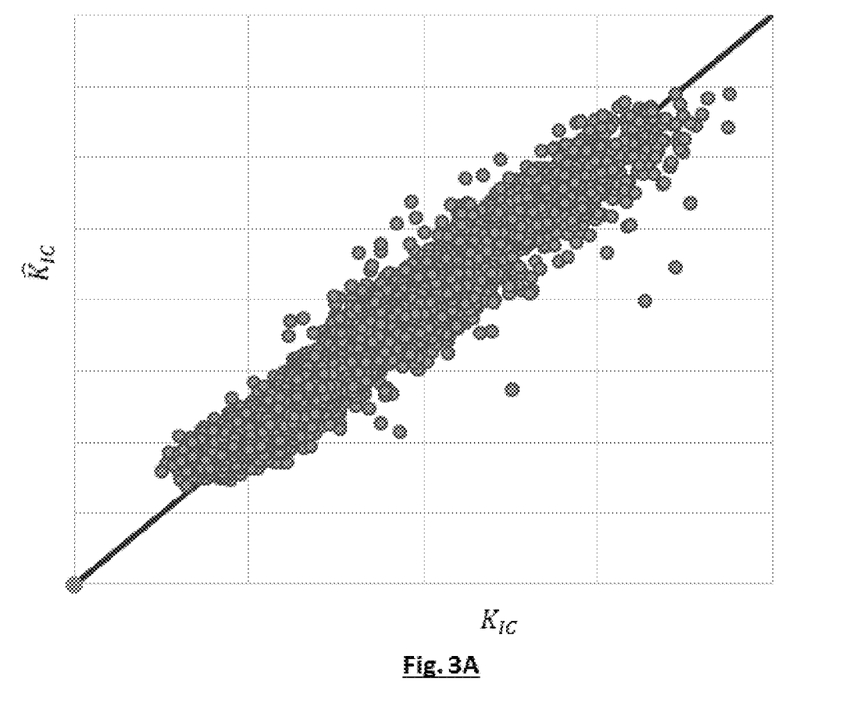
FIG. 3A represents fracture toughness values (critical value of the stress intensity factor) estimated by a neural network type model according to measured values.

The algorithm having been parameterized by the training set, tests aimed at evaluating the precision of the algorithm, that is to say the difference between the measured fracture toughness and the estimated fracture toughness, were carried out. FIG. 3A shows a curve, each point of which corresponds to a test sample. The abscissa and ordinate axes correspond respectively to fracture toughness ($K_{IC}$) values measured and estimated by the algorithm. We observe that the scatter around the line of equation y=x is weak. The curve in FIG. 3A was created considering test samples in all directions and of different thicknesses, ranging from 30 to 200 mm.

Figure 3B:
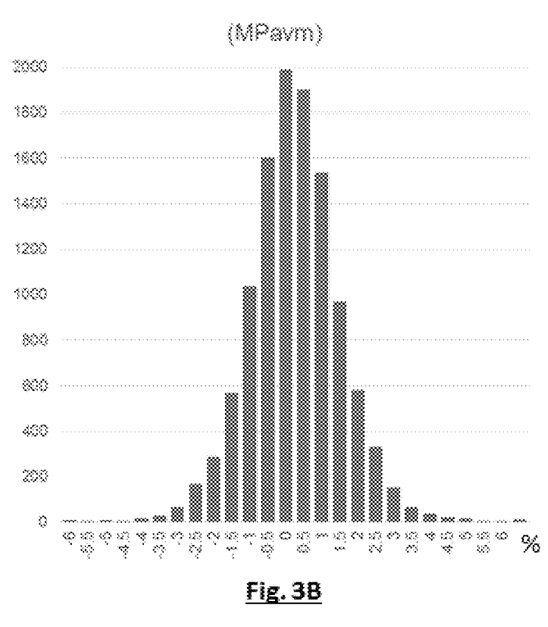
FIG. 3B shows a histogram of the relative fracture toughness estimation errors.

FIG. 3B corresponds to a histogram of relative errors (in %) between the fracture toughness values respectively measured and estimated by the algorithm. This histogram serves to evaluate an estimation uncertainty of the algorithm. The standard deviation $\sigma_{KIC}$ of this histogram is estimated at 1.3 MPa√m, making it possible to quantify the estimation uncertainty.

Figure 4A:
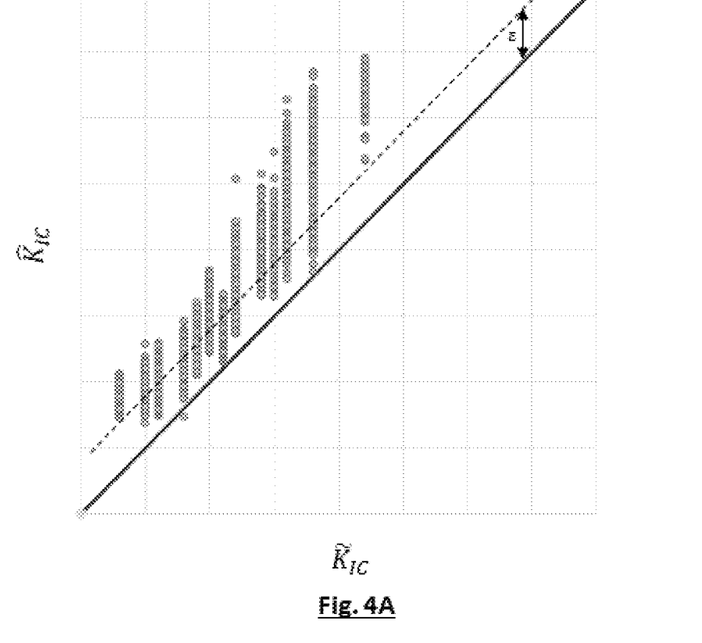
FIG. 4A represents consideration of a confidence interval, forming a safety margin, in the definition of an acceptance criterion, the latter corresponding to a fracture toughness value.
Figure 4B:
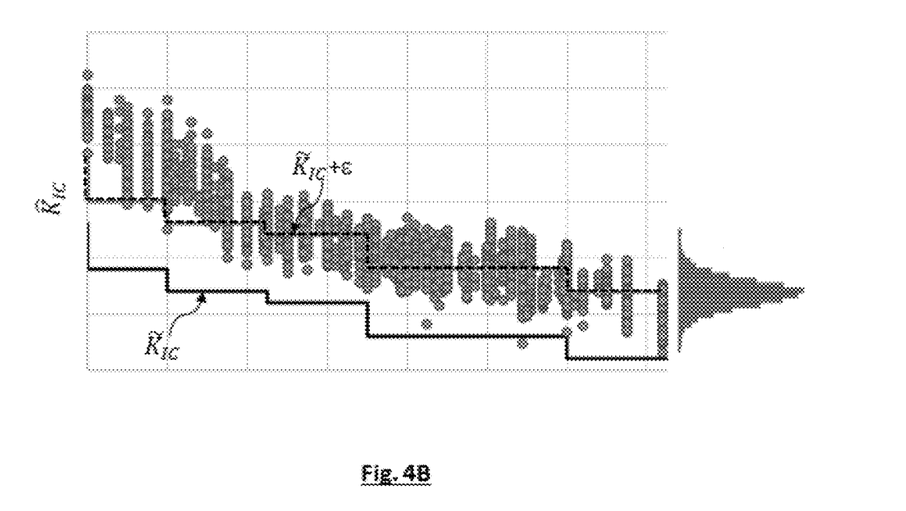
FIG. 4B illustrates, for different part thicknesses, the consideration of a confidence interval, forming a safety margin, with respect to an acceptance criterion.

FIG. 4A is a graph representing on the abscissa a required fracture toughness value, this value being for example derived from a specification by a constructor. On the ordinate, fracture toughness values estimated by the algorithm are represented. The solid line corresponds to the line of equation y=x. A dotted line has been drawn whose deviation from the line y=x corresponds to consideration of a margin of error, forming a confidence interval. According to a usual definition, the confidence interval corresponds to n times the standard deviation $\sigma_{KIC}$, where n is a positive real number. n can be for example equal to 2.

This graph illustrates how the uncertainty associated with the fracture toughness estimate can be taken into account to ensure compliance with a requirement resulting from a specification. $n \times \sigma_{KIC}$ corresponds to the confidence interval applied so as to take into account the uncertainty associated with the estimate. Thus, if $\tilde{K}_{IC}$ corresponds to an acceptance threshold of fracture toughness, defined in a specification, and if $\hat{K}_{IC}$ corresponds to the estimated fracture toughness resulting from the algorithm, compliance with the specification can be such that:
if

[Math]

$$\tilde{K}_{IC} + n \times \sigma_{KIC} \leq \hat{K}_{IC} \quad (2)$$

then the test sample is considered to conform to the acceptance threshold defined in the specification: the part thus passes the test.
If

[Math]

$$\tilde{K}_{IC} + n \times \sigma_{KIC} > \hat{K}_{IC} \quad (3)$$

then the test sample is considered not to conform to the acceptance threshold defined in the specification: based on the $\hat{K}_{IC}$ estimate, the part fails the test.

Thus, in general, it is possible to evaluate, from the test set, a statistical indicator $\sigma_{KIC}$ representative of the scatter of fracture toughness estimates $\hat{K}_{IC}$ with respect to the exact fracture toughness values. The statistical indicator serves to define a confidence interval $\varepsilon = n \times \sigma_{KIC}$ which is:
either added to the acceptance threshold $\tilde{K}_{IC}$, in which case the value $\tilde{K}_{IC} + \varepsilon$ is compared to the estimate $\hat{K}_{IC}$.

or subtracted from the estimate $\hat{K}_{IC}$, in which case the value $\hat{K}_{IC} - \varepsilon$ is compared to the acceptance threshold $\breve{K}_{IC}$.

FIG. 3B shows a generalization of this method on test samples of different thicknesses Th, with each thickness corresponding to a specification of fracture toughness $\breve{K}_{IC,Th}$. Each threshold value $\breve{K}_{IC,Th}$ is increased by ε. Test samples with an estimated fracture toughness less than $\breve{K}_{IC} + \varepsilon$ are considered non-compliant. The confidence interval may depend on the thickness.

Test samples considered to be non-compliant may be subject to an experimental determination of their fracture toughness, in order to determine their compliance or non-compliance with the specification defining the acceptance threshold. The experimental measurement is carried out by taking a test specimen from the test part. The fracture toughness value resulting from the experimental measurement is then again compared to the acceptance threshold $\breve{K}_{IC}$.

It is understood that the method serves to avoid carrying out an experimental fracture toughness measurement for all the parts such that:

[Math]

$$\breve{K}_{IC} + \varepsilon \leq \hat{K}_{IC} \quad (4)$$

Figure 4C:
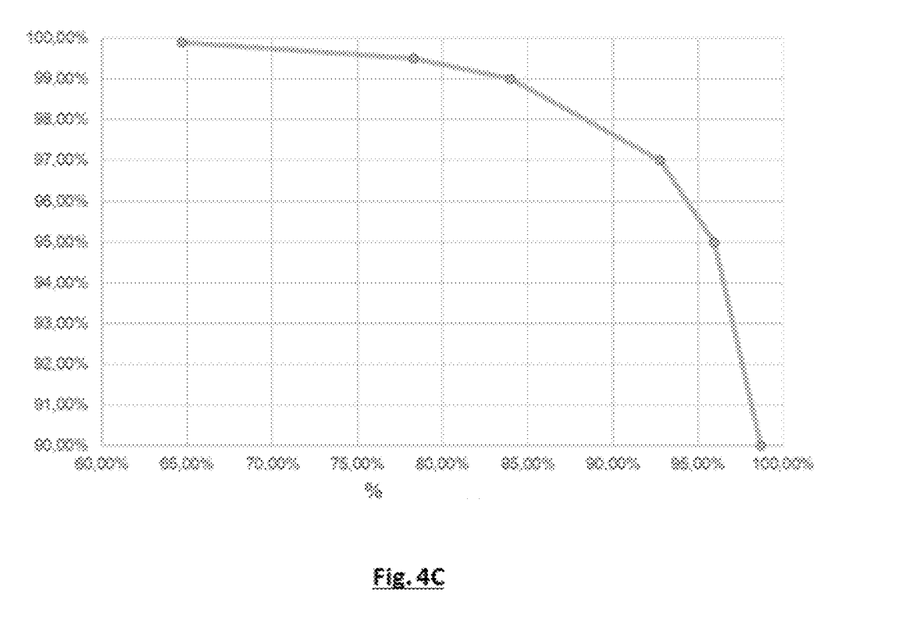
FIG. 4C represents a definition of a confidence level, defined from the confidence interval, according to a risk level.

The higher the value of n, the lower the percentage of avoided tests. FIG. 4C represents the percentage of tests avoided according to a confidence level associated with the confidence interval E, this latter corresponding to $n \times \sigma_{KIC}$. A 100% confidence level leads to an experimental measurement being carried out on all the test samples.

Figure 4D:
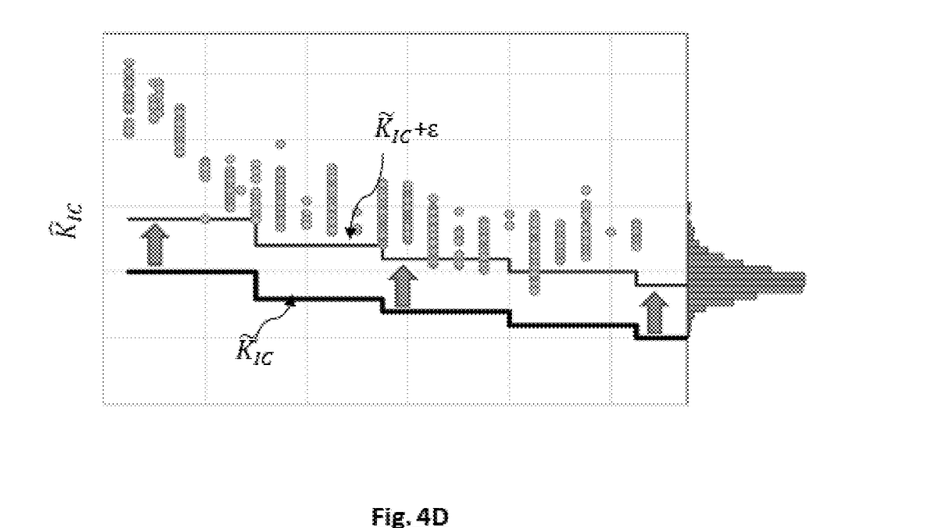
FIG. 4D illustrates, for different part thicknesses, the consideration of a safety margin with respect to a specification, using estimates of the fracture toughness of type AA7050 aluminum alloys.

FIGS. 3A, 3B and 4A to 4C were created considering a type AA2050 aluminum alloy. FIG. 4D is analogous to FIG. 4C, considering a type AA7050 aluminum alloy.

Figure 2B:
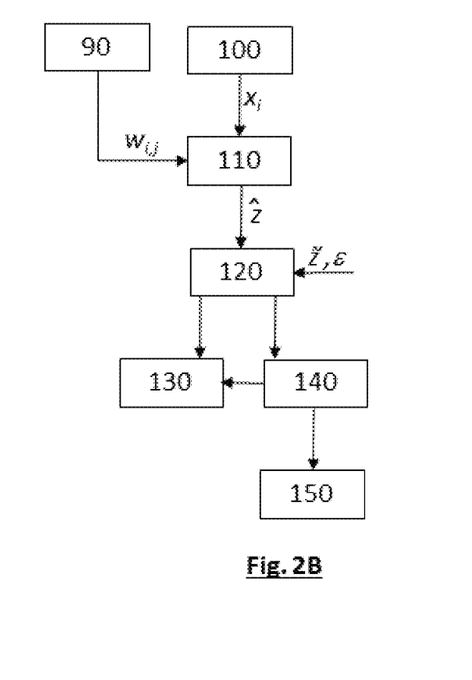
FIG. 2B represents the main steps of a procedure which is the subject of the invention.

FIG. 2B summarizes the main steps of a method for testing a part according to the invention.

Step 100: determination of the input parameters $x_i$ of the algorithm. All or part of the input parameters are determined experimentally.

Step 110: implementation of the algorithm, such as to obtain a value of the output variable $\hat{z}$ corresponding to an estimate of the damage tolerance property considered. In the examples given in connection with FIGS. 3A, 3B, 4A to 4C, $\hat{z} = \hat{K}_{IC}$ Step 120: consideration of a confidence interval ε and of an acceptance threshold $\breve{z}$. Comparison of the estimated property $\hat{z}$ with the acceptance threshold $\breve{z}$ taking into account the confidence interval ε. This latter is either subtracted from the estimated property $\hat{z}$ or added to the acceptance threshold $\breve{z}$.

Based on the comparison:
Step 130: acceptance of the test part; or
Step 140: Experimental determination of the damage tolerance property z, based on which the part is either accepted (step 130) or rejected (step 150).

The algorithm used in step 110 has previously been trained, using learning test samples. Learning is the subject of a step 90, during which the number of hidden layers, the number of nodes per hidden layer and the activation functions associated with the nodes of the hidden layer are defined. Learning comprises an optimization, used to define the weighting factors for each given pair of input $x_i$-node $y_j$ along with the bias $w_{0,j}$ associated with each node.

For AA2050 alloy sheets, the inventors were able to estimate the predictive power of the various input variables $x_i$ considered. Table 1 shows, for each input datum, the predictive power. This is a real number between 0 and 1, quantifying the relative importance of each input datum in the estimation of the result.

TABLE 1

| Input variable $x_i$ | Predictive power |
| --- | --- |
| Elongation at rupture | 0.88 |
| Yield strength | 0.57 |
| Thickness | 0.36 |
| Tensile strength | 0.16 |
| Li (%) | 0.08 |
| Cu (%) | 0.07 |

The input variables with the greatest influence on the estimation of fracture toughness are therefore the elongation at rupture, yield strength and thickness. The mass fractions of lithium and copper are of almost negligible significance in determining the mass fraction.

Figure 5A:
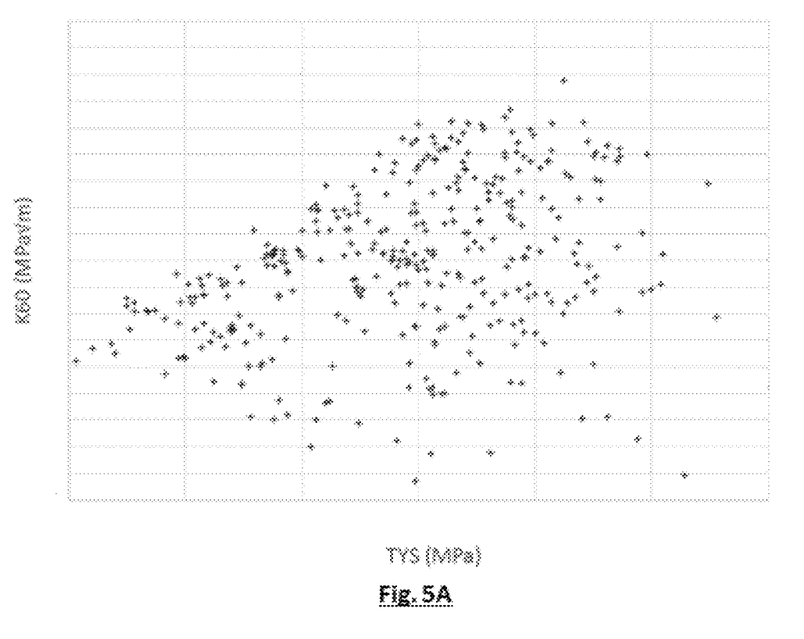

The inventors have developed an estimator, similar to that described above, capable of estimating intensity factors such as the apparent stress intensity factor $K_{app}$ or the intensity factor $K_{R60}$ defined beforehand. FIG. 5A represents a variation of the yield strength (abscissa axis) according to the intensity factor $K_{R60}$. Each cross corresponds to a test sample. As in FIG. 1, there is a certain correlation between the value of the yield strength and the value of the intensity factor $K_{R60}$.

Figure 5B:
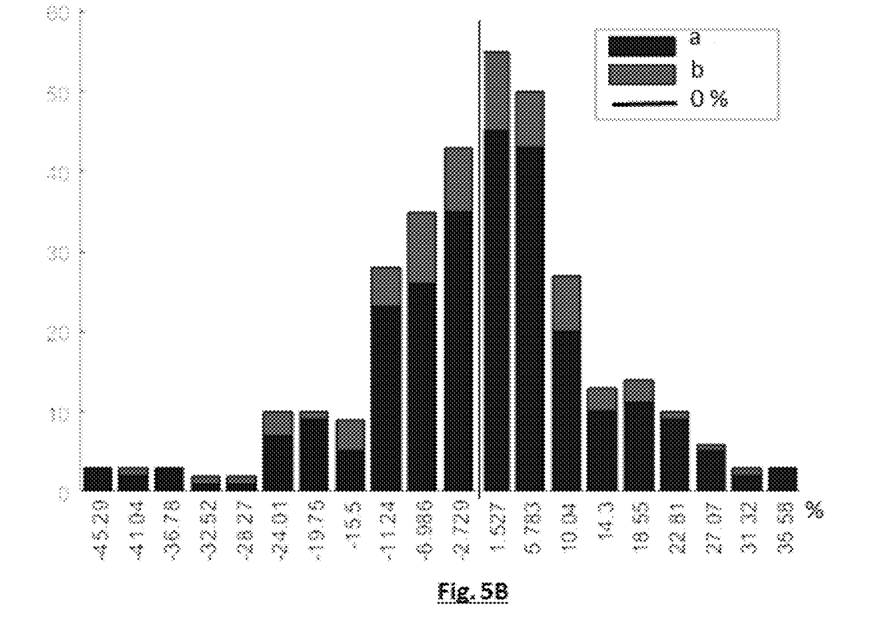
FIG. 5B shows a histogram of damage tolerance property estimation errors ($K_{app}$) on different types of aluminum alloy.
Figure 5C:
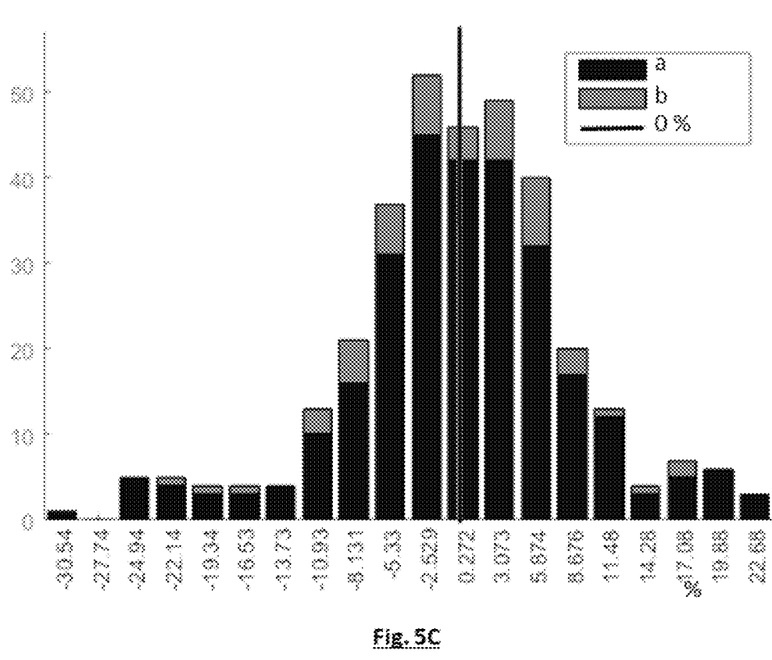
FIG. 5C shows a histogram of estimation errors of another damage tolerance property ($K_{R60}$) on different types of aluminum alloy.

FIGS. 5B and 5C represent a histogram of the relative errors (in %) of relative estimates of the apparent stress intensity factor and of the intensity factor $K_{R60}$. These histograms were produced from different types of alloy, which explains a greater scatter of the relative error values represented in FIG. 1B. In each of these figures, the dark gray levels (a) correspond to relative error values obtained using learning test samples, while the lighter gray levels (b) correspond to relative error values obtained using test samples. A straight line has also been shown corresponding to a zero relative error.

According to one embodiment, the input parameters of the estimation algorithm can include hardness values measured on the test part.

Further tests were performed to determine the influence of the input parameters on the accuracy of the fracture toughness estimate $\hat{K}_{IC}$. In these tests, the estimates of the fracture toughness $\hat{K}_{IC}$ were separated in the respective directions L-T, T-L and S-L. The directions considered were also taken into account when carrying out the tensile tests.

In one series of tests, the products analyzed were AA2050 T851 alloy sheets. The parameters of these tests are shown in Table 2A. The results of these tests are listed in Table 2B.

In Table 2A, the columns correspond respectively to the following data:
first column "Ref": reference of the test;
second column "Nb data": number of test samples considered. 80% of the test samples form the model learning set. 20% of the test samples form the test set;
third column "Thickness": consideration (X) or non-consideration of the thickness in the model;
fourth column "Widening": consideration (X) or non-consideration of a widening factor when widening is carried out during rolling;
fifth column "Orient": consideration of the orientation, as detailed in connection with tests 7 and 8
sixth, seventh and eighth columns: consideration (X) or non-consideration of properties resulting from tensile tests (UTS, TYS and A % respectively) in the L direction.
ninth, tenth and eleventh columns: consideration (X) or non-consideration of properties resulting from tensile tests (respectively UTS, TYS and A %) in the LT direction.

twelfth, thirteenth and fourteenth columns: consideration (X) or non-consideration of properties resulting from tensile tests (respectively UTS, TYS and A %) in the TS direction.

In Table 2B, the columns correspond respectively to the following data:
first column "Ref": reference of the test;
second, third and fourth columns: estimation (X) or non-estimation of fracture toughness respectively in the L-T, T-L and S-L directions;
fifth column: standard deviation of the estimation error;
sixth column: standard deviation of the relative estimation error;
seventh column: mean relative estimation error.

Data for estimation errors, shown in the fifth, sixth and seventh columns, are obtained as a result of the fracture toughness estimate with each test set.

In tests 1, 2 and 3, three estimators were developed and used, each estimator being respectively dedicated to the estimation of fracture toughness according to the directions L-T, T-L and S-L, from tensile strength data respectively measured according to the L, LT and ST directions. Each estimator took into account the thickness of the part. During test 1, the estimator was configured using tensile strength data measured along the L direction. The estimator thus configured was used to estimate the fracture toughness along the L-T directions. In test 2, the estimator was configured using tensile strength data measured in the LT direction. The estimator thus configured was used to estimate the fracture toughness according to the T-L directions. In test 3, the estimator was configured using tensile strength data measured in the ST direction. The estimator thus configured was used to estimate the fracture toughness according to the S-L directions. The estimates are correct, with an mean error of less than 4%.

In tests 4, 5 and 6, three estimators were developed and used, respectively serving to estimate the fracture toughness according to the three directions L-T, T-L and S-L, from tensile strength data measured in the three directions L, LT and ST. The estimators also took into account the thickness of the part.

It is observed that tests 4, 5 and 6 lead to reduced estimation errors compared to tests 1, 2 and 3. This shows that, in order to estimate a fracture toughness value in a given direction (for example the L-T direction), it is preferable to have input parameters, resulting from tensile tests, not in a single direction (in this case L for direction L-T), but in three directions (L, LT and ST). Thus, taking into account tensile strength data measured in multiple directions, such as two or three different directions, reduces the error in estimating fracture toughness, regardless of the directions considered for estimating fracture toughness.

In tests 7 and 8, the same estimator was used, developed with tensile test data from three directions (L, LT and ST). In test 8, the thickness of the part and the post-rolling widening factor were taken into account. During test 7, part thickness was not taken into account. When implementing the estimator, the operator selected the directions (L-T, T-L or S-L), corresponding to column 6 of the table:
when the selected direction is L-T, the input parameters are the tensile strength properties measured in the L direction;
when the selected direction is T-L, the input parameters are the tensile strength properties measured in the LT direction;
when the selected direction is S-L, the input parameters are the tensile strength properties measured in the ST direction.

We see that taking part thickness into account reduces the estimation error.

It follows from the above that it is optimal to take into account the thickness of the test part, along with the tensile strength properties in various directions. This reduces the estimation error and increases the repeatability of the measurements.

In one series of tests, the products analyzed were AA7050 T7451 alloy sheets. The parameters of these tests are shown in Table 3A. The results of these tests are listed in Table 3B. The columns of tables 3A and 3B contain the same data as the columns of tables 2A and 2B respectively.

Tests 9, 10 and 11 are similar to tests 1, 2 and 3 previously described in relation to Tables 2A and 2B.

Test 12 is similar to test 8, as the widening factor was not taken into account. Test 12 serves as a benchmark for comparison to tests 13 to 17. In tests 13 to 17, the estimator was configured and used without taking into account at least one of the parameters considered in test 12:
in test 13, part thickness was not taken into account;
in test 14, elongation at rupture was not taken into account;
in test 15, tensile strength was not taken into account;
in test 16, yield strength was not taken into account;
in test 17, tensile strength and yield strength were not taken into account.

It follows from tests 12 to 17 that failure to take into account tensile strength properties increases the estimation error. It appears particularly optimal to consider the three mechanical traction properties (tensile strength, yield strength and elongation at rupture), along with the thickness of the part. Moreover, the mechanical traction properties must be determined in a direction conducive to the directions considered to estimate fracture toughness: in this case L, LT and ST to estimate fracture toughness in the L-T, T-L and S-T directions respectively.

The invention serves to avoid systematic use of destructive tests on test specimens, which are reserved for parts whose estimated damage tolerance value is not sufficiently far from the acceptance threshold, with a predetermined level of confidence. It paves the way for a new approach to part testing for high-demand applications, such as vehicles or aircraft.

In another test series no. 18 (see Table 4), the product analyzed was AA 5083 H131 alloy plates for which the ballistic limit velocity (V50) was estimated taking into account the mid-thickness traction characteristics in the TL direction, i.e. yield strength, tensile strength and elongation measured at mid-thickness in the TL direction. The results obtained are given in Table 4. In Table 4, the columns correspond respectively to the following data:
first column "Ref": reference of the test;
second column: number of data taken into account, here 448,
third, fourth, fifth and sixth columns: parameters taken into account (X);
seventh column: type of values estimated, here the ballistic limit velocity (V50);
eighth column: standard deviation of the estimation error;
Ninth column: standard deviation of the relative estimation error;
Tenth column: mean relative estimation error.

It is thus shown that the previously described fracture toughness determination approach applies to the ballistic limit velocity (V50). It is also remarkable that the standard deviation of the relative error is small, indicating an excellent prediction by the method.

TABLE 2A

| Ref. | Nb data | Thickness | Widening | Orient. | L UTS | L TYS | L A% | LT UTS | LT TYS | LT A% | TS UTS | TS TYS | TS A% |
|---|---|---|---|---|---|---|---|---|---|---|---|---|---|
| 1 | 6435 | X | | | X | X | X | | | | | | |
| 2 | 6434 | X | | | | | | X | X | X | | | |
| 3 | 5544 | X | | | | | | | | | X | X | X |
| 4 | 6433 | X | | | X | X | X | X | X | X | X | X | X |
| 5 | 6432 | X | | | X | X | X | X | X | X | X | X | X |
| 6 | 5543 | X | | | X | X | X | X | X | X | X | X | X |
| 7 | 18321 | | | X | X | X | X | | | | | | |
|   |       | | | X | | | | X | X | X | | | |
|   |       | | | X | | | | | | | X | X | X |
| 8 | 18321 | X | X | X | X | X | X | | | | | | |
|   |       | | | X | | | | X | X | X | | | |
|   |       | | | X | | | | | | | X | X | X |

TABLE 2B

| Ref. | L-T KIC/Kq | T-L KIC/Kq | S-L KIC/Kq | σ(ε) | σ(ε) (%) | Mean(ε) (%) |
|---|---|---|---|---|---|---|
| 1 | X | | | 1.64 | 4.65 | 3.60 |
| 2 | | X | | 1.02 | 3.46 | 2.69 |
| 3 | | | X | 1.31 | 5.17 | 4.02 |
| 4 | X | | | 1.42 | 4.03 | 3.07 |
| 5 | | X | | 0.91 | 3.12 | 2.40 |
| 6 | | | X | 1.24 | 4.91 | 3.80 |
| 7 | X | | | 1.65 | 5.31 | 4.07 |
|   | | X | | | | |
|   | | | X | | | |
| 8 | X | | | 1.26 | 4.19 | 3.17 |
|   | | X | | | | |
|   | | | X | | | |

TABLE 3A

| Ref. | Nb data | Thickness | Widening | Orient. | L UTS | L TYS | L A% | LT UTS | LT TYS | LT A% | TS UTS | TS TYS | TS A% |
|---|---|---|---|---|---|---|---|---|---|---|---|---|---|
| 9 | 1480 | X | | | X | X | X | | | | | | |
| 10 | 1480 | X | | | | | | X | X | X | | | |
| 11 | 1480 | X | | | | | | | | | X | X | X |
| 12 | 4440 | X | | X | X | X | X | | | | | | |
|    |      | | | X | | | | X | X | X | | | |
|    |      | | | X | | | | | | | X | X | X |
| 13 | 4440 | | | X | X | X | X | | | | | | |
|    |      | | | X | | | | X | X | X | | | |
|    |      | | | X | | | | | | | X | X | X |
| 14 | 4440 | X | | X | X | X | | | | | | | |
|    |      | | | X | | | | X | X | | | | |
|    |      | | | X | | | | | | | X | X | |
| 15 | 4440 | X | | X | | X | X | | | | | | |
|    |      | | | X | | | | | X | X | | | |
|    |      | | | X | | | | | | | | X | X |
| 16 | 4440 | X | | X | X | | X | | | | | | |
|    |      | | | X | | | | X | | X | | | |
|    |      | | | X | | | | | | | X | | X |
| 17 | 4440 | X | | X | | X | | | | | | | |
|    |      | | | X | | | | | X | | | | |
|    |      | | | X | | | | | | | | X | |

TABLE 3B

| Ref. | L-T KIC/Kq | T-L KIC/Kq | S-L KIC/Kq | σ(ε) | σ(ε) (%) | Mean(ε) (%) |
|---|---|---|---|---|---|---|
| 9 | X | | | 0.94 | 2.74 | 2.04 |
| 10 | | X | | 0.88 | 2.91 | 2.16 |
| 11 | | | X | 1.17 | 3.63 | 2.85 |
| 12 | X | | | 1.23 | 3.76 | 2.96 |
|    | | X | | | | |
|    | | | X | | | |
| 13 | X | | | 1.58 | 4.74 | 3.70 |
|    | | X | | | | |
|    | | | X | | | |
| 14 | X | | | 1.29 | 3.95 | 3.11 |
|    | | X | | | | |
|    | | | X | | | |

TABLE 3B-continued

| Ref. | L-T KIC/Kq | T-L KIC/Kq | S-L KIC/Kq | σ(ε) | σ(ε) (%) | Mean(ε) (%) |
|---|---|---|---|---|---|---|
| 15 | X | X | X | 1.34 | 4.08 | 3.20 |
| 16 | X | X | X | 1.29 | 3.93 | 3.08 |
| 17 | X | X | X | 1.36 | 4.16 | 3.27 |

TABLE 4

| | | Inputs | | | Target | (σ) | | Mean |
|---|---|---|---|---|---|---|---|---|
| REF | Nb data | Th. | UTS (LT) | TYS (LT) | A % (LT) | V50 (m/s) | Value (m/s) | (%) | (ε) (%) |
| 18 | 448 | X | X | X | X | X | 0.28 | 0.039 | 0.05 |

The invention claimed is:

1. A method for testing a damage-tolerant property in an aluminum alloy part, the part being in the shape of a metal sheet or extruded profile, said method comprising
   a) measuring at least two properties resulting from tensile testing of the part, in L (longitudinal) and/or ST (short transverse) and/or LT (long transverse) directions, the properties being chosen from:
      yield strength;
      and/or tensile strength;
      and/or elongation at rupture;
   b) take into account a thickness of the part;
   c) using properties measured during a) along with the thickness taken into account during b) as input parameters (xi) for a neural network estimator;
   d) estimating, using the neural network estimator, a property representative of the part's damage tolerance ($\hat{z}$, $\hat{K}_{IC}$);
   e) taking into account an acceptance threshold ($\tilde{z}$, $\tilde{K}_{IC}$) and a confidence interval (ε) and comparing a property estimated ($\hat{z}$, $\hat{K}_{IC}$) during d) to the acceptance threshold, taking into account the confidence interval;
   f) based on the comparison:
      consider whether said part passes the test;
      or consider whether said part does not pass the test.

2. The method according to claim 1, in which when, during f), said part fails the test, the method comprises g) measuring damage tolerance property of the part from a test specimen taken from said part.

3. The method according to claim 1 in which c) also comprises taking into account a concentration of at least one alloy element in the aluminum alloy.

4. The method according to claim 1, in which the a) comprises measuring elongation at rupture and in which c) involves taking into account elongation at rupture thus measured.

5. The method according to claim 4, in which a) comprises measuring yield strength and in which c) comprises taking into account yield strength thus measured.

6. The method according to claim 1, in which c) also comprises consideration of a hardness property.

7. The method according to claim 1, in which a) consists of only measuring elongation at rupture and yield strength, and in which c) comprises consideration of elongation at rupture and yield strength thus measured.

8. The method according to claim 1 in which:
   when d) comprises the estimation of the property representative of the damage tolerance of the part according to the L-T (Longitudinal—Long Transverse) directions, c) comprises, at least, consideration of one or more properties measured during a), in direction L;
   when d) comprises the estimation of the property representative of the damage tolerance of the part according to the T-L (Long Transverse—Longitudinal) directions, c) comprises, at least, consideration of one or more properties measured during a), in direction LT;
   when d) comprises an estimation of the property representative of a damage tolerance of the part according to the S-L (Short Transverse—Longitudinal) directions, c) comprises, at the least, consideration of the properties measured during a), in direction ST.

9. The method according to claim 1 in which c) involves consideration of properties measured during a), in several directions.

10. The method according to claim 9, in which c) involves taking into account three properties measured in a), in three different directions.

11. The method according claim 1, in which the damage tolerance property is an apparent intensity factor or a critical value of an intensity factor also called fracture toughness, or an effective stress intensity factor for a predetermined effective crack extension, using optionally 60 mm ($K_{R60}$).

12. The method according to claim 1, in which the damage tolerance property is a ballistic limit velocity (V50).

13. The method according to claim 1, in which the aluminum alloy is an alloy of the 2XXX series, or the 7XXX series, or the 6XXX series, or the 5XXX series.

14. The method according to claim 1, in which c) is implemented by a processing unit, optionally a microprocessor.

* * * * *